(12) United States Patent
Buerger et al.

(10) Patent No.: US 10,993,665 B1
(45) Date of Patent: May 4, 2021

(54) NEURAL INTERFACE METHODS AND APPARATUS TO PROVIDE ARTIFICIAL SENSORY CAPABILITIES TO A SUBJECT

(71) Applicant: National Technology & Engineering Solutions of Sandia, LLC, Albuquerque, NM (US)

(72) Inventors: Stephen P. Buerger, Albuquerque, NM (US); Kenneth E. Wojciechowski, Cupertino, CA (US); Roy H. Olsson, Arlington, VA (US); Deepesh K. Kholwadwala, Albuquerque, NM (US); David K. Novick, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 534 days.

(21) Appl. No.: 15/411,644

(22) Filed: Jan. 20, 2017

Related U.S. Application Data

(63) Continuation of application No. 12/136,859, filed on Jun. 11, 2008, now Pat. No. 9,549,704.

(51) Int. Cl.
  *A61B 5/00* (2006.01)
  *A61B 5/24* (2021.01)
  (Continued)

(52) U.S. Cl.
  CPC .......... *A61B 5/6847* (2013.01); *A61B 5/0031* (2013.01); *A61B 5/24* (2021.01);
  (Continued)

(58) Field of Classification Search
  CPC . A61B 5/6847; A61B 5/4836; A61B 5/04012; A61B 5/04001; A61B 5/0478; A61B 5/0031
  See application file for complete search history.

(56) References Cited

U.S. PATENT DOCUMENTS

| | | |
|---|---|---|
| 5,314,495 A | 5/1994 | Kovacs |
| 5,387,259 A | 2/1995 | Davidson |

(Continued)

OTHER PUBLICATIONS

Buerger, S. et al., "Portable, Chronic Neural Interface System Design for Sensory Augmentation," Proceedings of the IEEE/EMBS conference on Neural Engineering, Kohala Coast, HI, USA, May 2-May 5, 2007.

(Continued)

*Primary Examiner* — Rex R Holmes
(74) *Attorney, Agent, or Firm* — Daniel J. Jenkins

(57) ABSTRACT

Embodiments of neural interfaces according to the present invention comprise sensor modules for sensing environmental attributes beyond the natural sensory capability of a subject, and communicating the attributes wirelessly to an external (ex-vivo) portable module attached to the subject. The ex-vivo module encodes and communicates the attributes via a transcutaneous inductively coupled link to an internal (in-vivo) module implanted within the subject. The in-vivo module converts the attribute information into electrical neural stimuli that are delivered to a peripheral nerve bundle within the subject, via an implanted electrode. Methods and apparatus according to the invention incorporate implantable batteries to power the in-vivo module allowing for transcutaneous bidirectional communication of low voltage (e.g. on the order of 5 volts) encoded signals as stimuli commands and neural responses, in a robust, low-error rate, communication channel with minimal effects to the subjects' skin.

4 Claims, 7 Drawing Sheets

Related U.S. Application Data

(60) Provisional application No. 61/040,168, filed on Mar. 28, 2008.

(51) Int. Cl.
*A61B 5/291* (2021.01)
*A61B 5/316* (2021.01)

(52) U.S. Cl.
CPC .............. *A61B 5/291* (2021.01); *A61B 5/316* (2021.01); *A61B 5/4836* (2013.01)

(56) References Cited

U.S. PATENT DOCUMENTS

| | | | |
|---|---|---|---|
| 6,885,753 | B2 | 4/2005 | Bank |
| 7,308,314 | B2 | 12/2007 | Havey et al. |
| 7,751,877 | B2 | 7/2010 | Flaherty et al. |
| 7,881,780 | B2 | 2/2011 | Flaherty |
| 7,894,905 | B2 | 2/2011 | Pless et al. |
| 8,626,302 | B2 | 1/2014 | Bennett et al. |
| 8,812,096 | B2 | 8/2014 | Flaherty et al. |
| 2002/0077563 | A1* | 6/2002 | Sweeney .............. A61B 5/0031 600/510 |
| 2005/0143589 | A1 | 6/2005 | Donoghue et al. |
| 2005/0283203 | A1 | 12/2005 | Flaherty et al. |
| 2006/0049957 | A1 | 3/2006 | Surgenor et al. |
| 2006/0052826 | A1 | 3/2006 | Kim et al. |
| 2006/0052827 | A1 | 3/2006 | Kim et al. |
| 2006/0052837 | A1 | 3/2006 | Kim et al. |
| 2006/0149338 | A1 | 7/2006 | Flaherty et al. |
| 2006/0167564 | A1 | 7/2006 | Flaherty et al. |
| 2006/0173259 | A1 | 8/2006 | Flaherty et al. |
| 2006/0241356 | A1 | 10/2006 | Flaherty |
| 2006/0253161 | A1 | 11/2006 | Libbus |
| 2007/0167867 | A1 | 7/2007 | Wolf |
| 2007/0203533 | A1 | 8/2007 | Goren |
| 2007/0239211 | A1* | 10/2007 | Lorincz .............. A61N 1/37288 607/2 |
| 2008/0058874 | A1* | 3/2008 | Westlund .............. A61B 5/1104 607/2 |
| 2008/0177196 | A1 | 7/2008 | Burdick et al. |
| 2016/0167530 | A1 | 6/2016 | Bolik et al. |

OTHER PUBLICATIONS

Mohseni, P. et al., "Wireless Multichannel Biopotential Recording Using an Integrated FM Telemetry Circuit," IEE Transactions on Neural Systems and Rehabilitation Engineering (2005) 13(3):263-271.

Harrison, R. et al., "A Low-Power Integrated Circuit for a Wireless 100-Electrode Neural Recording System," IEEE Journal of Solid-State Circuits (2007) 42(1):123-133.

Layton, J., "How BrainPort Works," [online] [retrieved on Jun. 21, 2007] retrieved from the Internet: science.howstuffworks.com/brainport.htm/printable, 7 pages.

Neuronexus Technologies, "Silicon Microelectrode Array Chronic Research Probe Catalog," Rev. 1.2 Jul. 2006, [online][retrieved on Jun. 20, 2007] retrieved from the Internet: www.neuronexustech.com/Products/catalog_chronic.pdf, 39 pages.

Allan, R., "Implants Bring Hope to the Toughest Medical Handicaps," Electronic Design, Jun. 29, 2007, [online] [retrieved on Jul. 2, 2007] retrieved from the Internet: www.elecdesign.com/articles/articleID/15868/15868.html, 8 pages.

* cited by examiner

NEURAL INTERFACE METHODS AND APPARATUS TO PROVIDE ARTIFICIAL SENSORY CAPABILITIES TO A SUBJECT

RELATED APPLICATIONS

This application is a continuation of U.S. Non-Provisional patent application Ser. No. 12/136,859, entitled NEURAL INTERFACE METHODS AND APPARATUS TO PROVIDE ARTIFICIAL SENSORY CAPABILITIES TO A SUBJECT, filed Jun. 11, 2008, granted as U.S. Pat. No. 9,549,704 B1 on Jan. 24, 2017 having the same title, and further claims the benefit of U.S. Provisional Application No. 61/040,168 filed on Mar. 28, 2008, the entireties of which are herein incorporated by reference.

STATEMENT REGARDING FEDERALLY SPONSORED RESEARCH OR DEVELOPMENT

The United States Government has certain rights in this invention pursuant to Department of Energy Contract No. DE-AC04-94AL85000 with Sandia Corporation.

FIELD OF THE INVENTION

The invention generally relates to bidirectionally communicating neural interfacing methods and apparatus for providing artificial sensory capabilities to a subject that comprise sensing environmental attributes beyond the natural capability of a healthy subject and, obtaining neural responses from the subject. The invention further relates to neural interfacing methods and apparatus comprising environmental sensors in radio communication with an externally mounted (ex-vivo) module attached to and portable by the subject, that transcutaneously communicates neural stimulus commands via an inductively coupled link, to an internally mounted (in-vivo) module implanted in the subject. The invention additionally relates to methods and apparatus for low voltage, low error rate, encoded transcutaneous communication of neural stimulus commands and neural responses, utilizing an inductively coupled link.

BRIEF DESCRIPTION OF THE DRAWINGS

The accompanying drawings, which are incorporated in and form part of the specification, illustrate several embodiments of the present invention and, together with the description, serve to explain the principles of the invention. The drawings provided herein are not drawn to scale.

BACKGROUND

Figure 1:
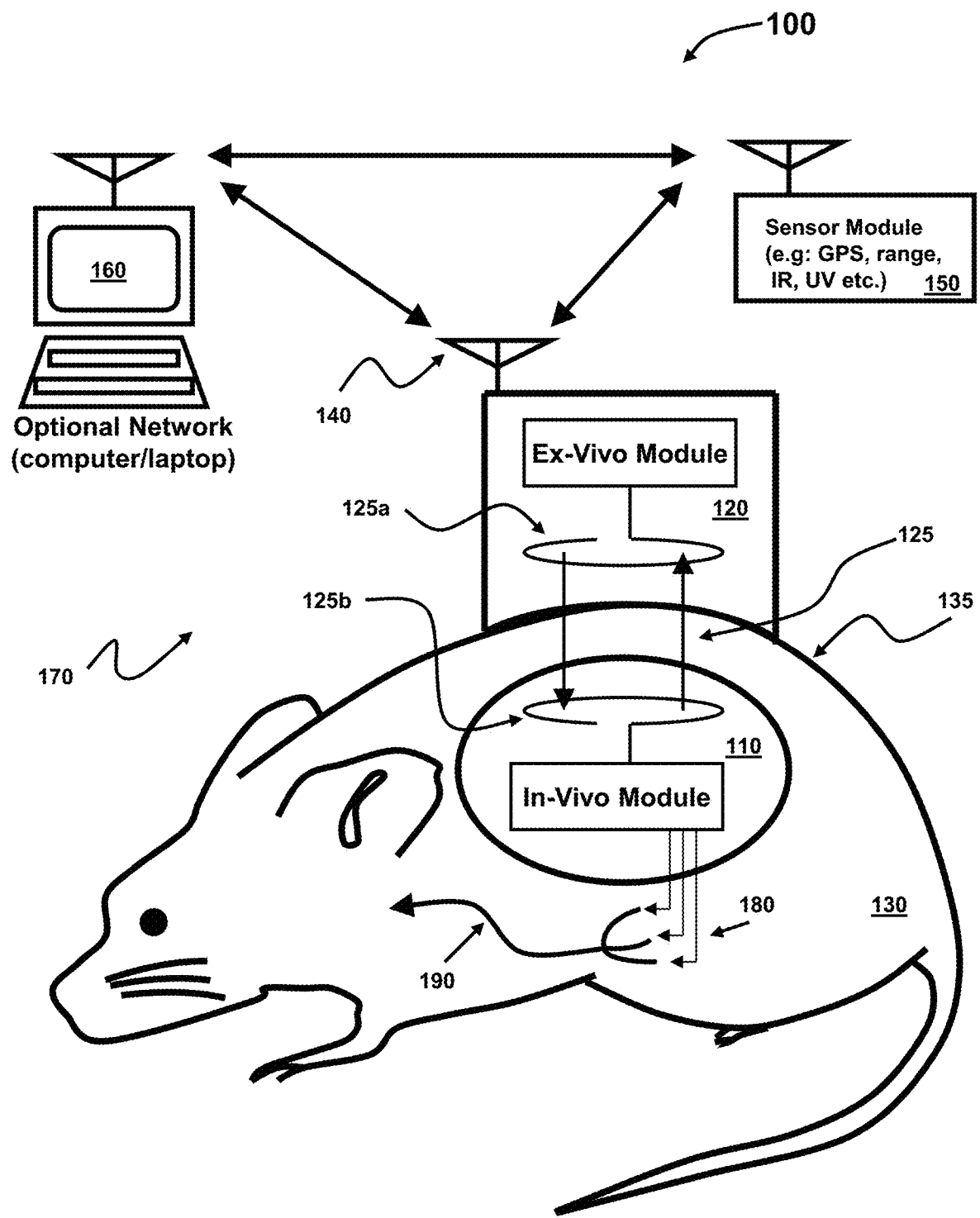
FIG. 1 is a schematic block diagram of an embodiment of a neural interface according to the present invention.

Prior work in neural interfaces is largely directed toward the restoration of lost natural capabilities or functions in amputees and victims of neurological injuries, e.g. the restoration or augmentation of the natural sensory capability of a subject. See for example: Buerger, S., et al., "Portable, Chronic Neural Interface System Design for Sensory Augmentation", Proceedings of the IEEE/EMBS conference on Neural Engineering, Kohala Coast, Hi., USA, May 2-5, 2007, the contents of which are incorporated herein in their entirety. In contrast, embodiments of the neural interface methods and apparatus according to the present invention are directed to providing an "artificial" sensory capability to a subject, which includes healthy subjects. The possibility of adding new capabilities (i.e. artificial sensory capabilities) to individuals (i.e. subjects) depends on a central hypothesis: That there exists sufficient and accessible excess capacity in the nervous system of an individual, to permit the performance of significant additional, unnatural functions without substantially interfering with the natural functions of the individuals' nervous system.

An artificial sensory capability is defined herein as providing to a subject, information pertaining to an environment within which the subject is operating, the information being obtained from sensors that are sensing environmental attributes beyond the natural sensory capability of the subject and, recording of neural responses from the subject. Within the context of the present invention, a neural interface includes apparatus and methods for conveying information obtained from environmental sensors to the subject, in the form of electrical neural stimuli applied to the nervous system of the subject.

For example, in a human or laboratory animal subject, artificial sensory capabilities can include providing the subject with the ability to sense wavelengths of light in the infra-red ("IR") and ultra-violet ("UV") spectrum (i.e. beyond the natural visible range of the subject) by interfacing the nervous system of the subject with input from IR or UV sensors. Other examples of an artificial sensory capability that can be provided to a subject include; i) the ability to sense a source of radiation through a neural interface to a radiation sensor, ii) the ability to sense range to a target as determined by a range sensing device (e.g. radar or sonar), iii) locational information provided by a positional sensor (e.g. global positioning system or "GPS"), iv) locational information pertaining to location and drift of a chemical plume as can be obtained from a plurality of chemical sensors, v) visual information in directions/locations that differ from the position/orientation of a subject's eyes, e.g. eyes in the back of the head, eyes at the end of a pole, vi) sound waves outside of the audible range in either frequency, volume or location, vii) sensor data indicating the location of or directional vector to specific (i.e. tagged) objects or other people, vii) sense of spatial direction such as from a compass or direction of a local reference, viii) sense of relative or absolute timing, and ix) sensors conveying status of (e.g. vital signs, cortisol levels, EEG measurements, galvanic skin response) or voluntary communication from other people or networks.

The sensed environment can include the physical environment containing the subject, or as well can comprise a virtual environment within which the subject is operating.

Virtual environments can include for example, electronically generated simulations (e.g. simulated environment) with which a subject interacts, as well as a remote environment (e.g. telepresence) through which a subject may remotely interact with physical objects. An example of the latter is in providing a subject with a remote presence, allowing intuitive control with instantaneous response to aid in guiding remotely-located vehicles or robots. For example, sensors located on a remotely guided vehicle can be configured to sense the forces and accelerations acting on the vehicle in real time (e.g. such as the effects of choppy air on an aerial vehicle) with this information being conveyed to the subject via an embodiment of a neural interface according to the present invention, thereby providing the subject with the intuitive feel of guiding the vehicle and a level of control not currently available as in conventional tele-operation of the vehicle. Other examples related to remotely controlled or simulated environments include sensory input related to proprioceptive or other feedback from remotely controlled robots or machines as well as data generated as the output of automated algorithms that monitor data and draw conclusions, e.g. software that monitors a broad set of sensor data and sends only certain information to the neural interface based on programmed algorithms.

Embodiments of the present invention comprise sensors for sensing environmental attributes beyond the natural sensing capability of the subject, and communicating those attributes to an externally mounted module attached to and portable by the subject (i.e. ex-vivo to the subject). The externally mounted module receives the environmental attributes and communicates the attributes to an internally mounted module within the subject (in-vivo to the subject). The internally mounted module converts the environmental information into electrical neural stimuli that are delivered through implanted electrodes (e.g. probes) to the nervous system of the subject, comprising either peripheral or central neurons. Embodiments of the present invention include the capability for bidirectional communication of neural stimuli and neural responses, between the nervous system of the subject, internal and external modules and (optional) external communication systems and networks.

Neural interfaces according to the present invention find application in many fields. In the military arena alone, conflicts are increasingly fought in confusing, complex environments that decrease the advantages brought by technology due to the unwieldiness of heavy weaponry, the proliferation of small arms and night vision technology, including the affect of an often-overwhelming amount of sensor data to digest. The enhancement of situational awareness for individual soldiers through a set of neurally-tied artificial sensors can provide a new advantage to soldiers operating in challenging environments and create new means of protection. Similarly, bidirectional neural interfaces can enable an advanced form of "remote presence" allowing intuitive control with instantaneous response to guide remotely-located vehicles, robots and prosthetic devices.

DETAILED DESCRIPTION OF THE INVENTION

Embodiments of methods and apparatus according to the present invention comprise sensors for sensing environmental attributes beyond the natural sensing capability of a subject, and communicating those attributes wirelessly via a radio frequency ("RF") link to an externally mounted module attached to the subject (i.e. ex-vivo to the subject). The externally mounted module receives the environmental attributes (e.g. as the magnitude of a sensed attribute) and communicates the attributes via an inductively coupled link, to an internally mounted module within the subject (in-vivo to the subject). The internally mounted module converts the environmental information into electrical neural stimuli that are delivered through one or more electrodes (e.g. probes) to the nervous system of the subject. An electrode can comprise one or more electrical contacts to sites (e.g. neurons) located within the nervous system of the subject. Embodiments of the present invention include the capability for bidirectional communication of neural stimuli and neural responses, between the nervous system of the subject and (optional) external communication systems and networks. Embodiments of neural interface methods and apparatus according to the present invention comprise a stimulating and recording nerve implant portion powered by a battery (i.e. in-vivo module), and an external, wearable, subject-portable portion (i.e. ex-vivo module) that communicates wirelessly with the implanted portion and environmental sensors, and can be further utilized to communicate with an external computer or communications network.

FIG. 1 is a schematic block diagram of an embodiment of a neural interface according to the present invention. FIG. 1 illustrates a non-limiting exemplary embodiment of a neural interface to the peripheral nervous system (PNS) of a subject. Embodiments of the invention are applicable to subjects that can range from a laboratory test animal as illustrated, through a human being. Neural interface 100 comprises an implantable in-vivo module 110, a subject-portable, external ex-vivo module 120 (e.g. a wearable portion, "belt pack", "backpack" etc.) that can be attached to the subject 130, by means such as straps, belts, tapes, adhesives etc. and, one or more sensors 150 that sense attributes of the environment 170. Information pertaining to the environmental attributes sensed by the sensor modules 150 can be wirelessly transmitted to the ex-vivo module 120, which receives and processes the information and further communicates the information to the in-vivo module 110. In-vivo module 110 additionally processes the information and, via one or more electrodes 180 provides the information as electrical neural stimuli to one or more sites (e.g. neurons) located on a peripheral nerve 190 (e.g. nerve bundle) within the subject 130, The external portion 120 communicates wirelessly and bidirectionally with the implanted portion 110 through a low voltage inductively coupled link 125, and can additionally communicate through a radio frequency (RF) link 140 to sensors 150 and (optional) external networks and computers 160 that can comprise a wireless network. Inductively coupled link 125 can comprise one or more coils mounted external to the subject (e.g. 125a) located proximal to one or more coils implanted in the subject (e.g. 125b). For example, coils comprising the inductive link 125 can be proximally mounted on either side of the subjects' skin 135.

Sensors 150 can be carried by the subject 130 (e.g. attached to the external module 120) or can as well be remotely located throughout an environment 170 (e.g. physical or virtual environment) within which the subject 130 is operating. Sensors 150 are configured to sense attributes of the environment 170 that are beyond the natural sensing capability of the subject 130. Sensors 150 can for example, be configured to sense range to an object, as for an acoustic range detector. Information pertaining to the range to an object can be transmitted wirelessly by sensor module 150 to the ex-vivo module 120 and optionally, to a networked computer 160.

Sensors 150 typically produce outputs in the form of amplitude-modulated voltages that are proportional to the magnitude of the sensed attribute. However, the nervous system of a subject 130 typically communicates signals as constant amplitude pulses called "action potentials", wherein the magnitude of the signal is proportional to the frequency (i.e. repetition rate) of the pulses. To achieve compatibility of a sensors' output with the peripheral nerve 190 of the subject 130, ex-vivo module 120 can be configured to translate the amplitude-modulated information received from the sensor module 150 into a frequency-modulated signal compatible with neural stimulation. To ensure accurate communication of this information to the in-vivo module 110, ex-vivo module 120 can further be configured to encode the frequency-modulated information (e.g. via frequency-shift-key, "FSK" encoding) and transmit the encoded information via the low-voltage inductive link 125 to the in-vivo module 110. The in-vivo module 110 can be configured to receive the encoded information, decode and convert the encoded information into electrical neural stimuli. An implanted electrode 180 connected to the en-vivo module 110 and contacting one or more sites along peripheral nerve 190 can be employed to deliver the electrical neural stimuli to the peripheral nerve 190.

The utilization of an implanted electrode 180 (e.g. a point electrode, an electrode array, a microelectromechanical (MEM) electrode array) to stimulate peripheral nerve 190 (e.g. a nerve or nerve bundle) avoids the use of percutaneous wires or connectors, reducing the risk of irritation and infection making embodiments of the present invention amenable to chronic (e.g. long-term) use. As described more fully below, embodiments according to the present invention include robust, low-error rate methods for bi-directional communication of encoded information between the ex-vivo module 120 and the in-vivo module 110 by means of the low-voltage inductively coupled link 125. The use of a low-voltage inductively coupled link 125, transmitting a signal on the order of 12 volts peak-to-peak or less (with embodiments expected to utilize approximately 5 volts peak-to-peak) avoids heating of the subjects' skin 135 during transdermal communication, and the deleterious effects to the skin 135 that can be caused by such heating. The low-voltage inductively coupled link 125 additionally enables the use of smaller, safer, lower-power electronics, facilitating portability by the subject. Further embodiments of, and the functionality of methods and apparatus according to the invention are discussed in detail below.

Figure 2:
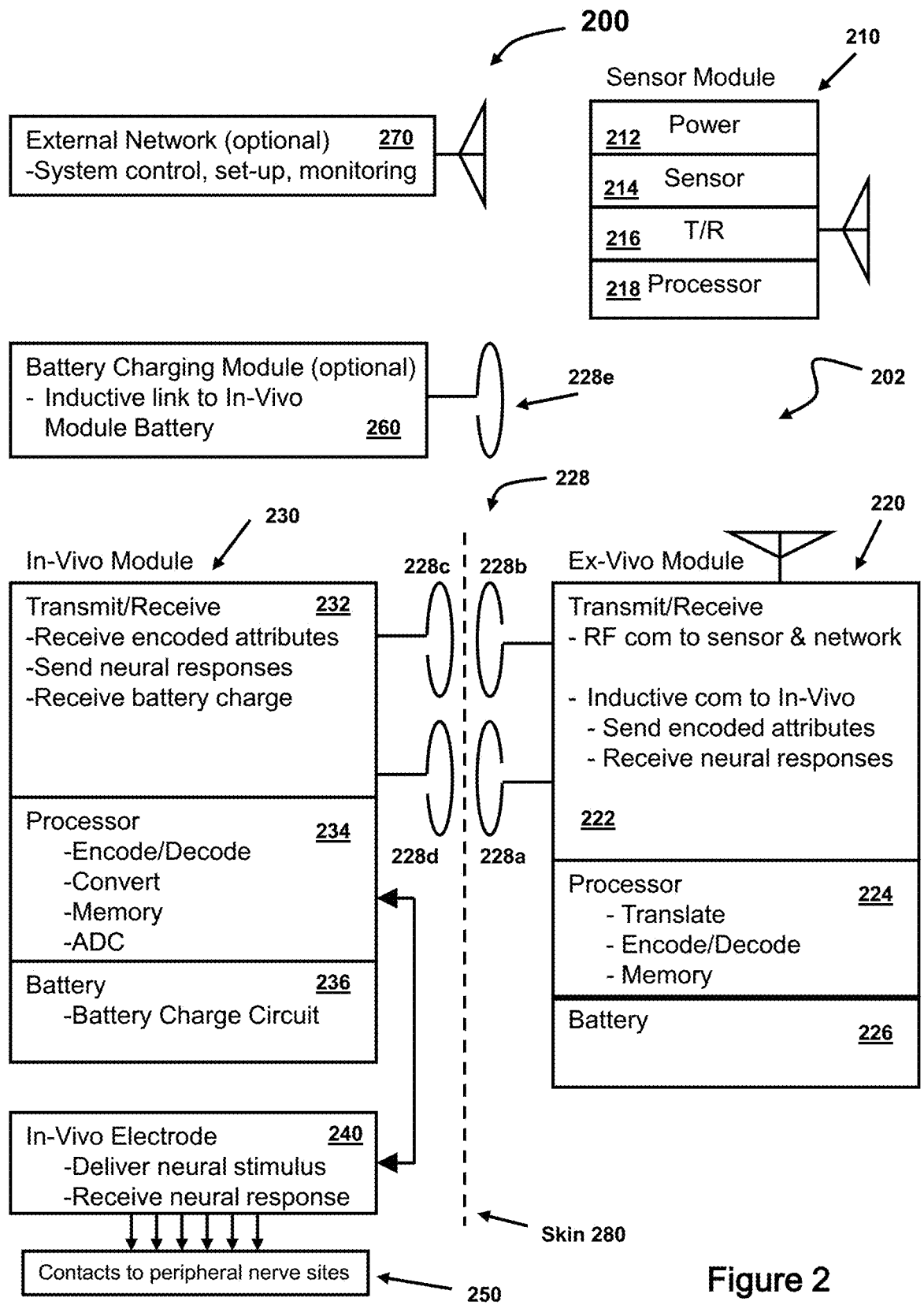
FIG. 2 is a schematic block diagram of another embodiment of a neural interface according to the present invention.

FIG. 2 is a schematic block diagram of another embodiment of a neural interface according to the present invention. Neural interface 200 comprises one or more sensor modules 210 arranged to sense attributes of an environment 202 within which a subject (not shown) is operating. Sensor module 210 can include sub-modules for power 212, a sensor element 214 for sensing environmental attributes, a processor module 218 and a transmit-receive ("T/R") module 216 for wirelessly transmitting the sensed attributes. Ex-vivo module 220, mounted externally to the subject can include transmit-receive sub-module 222 for communicating with sensor modules 210, optional external communication networks and computers 270 and, via an inductively coupled link 228 to in-vivo module 230. Inductively coupled link 228 can comprise coils mounted external to the subject (e.g. 228a,b) connected to the external transmit-receive sub-module 222, that are inductively coupled to internally mounted coils (e.g. 228c,d) connected to the internal transmit-receive sub-module 232. The internal (in-vivo) and external (ex-vivo) coils are preferably located proximal to each other on opposed sides of the subject's skin 280.

In an exemplary embodiment, sensor module 210 can comprise an analog voltage output ultrasonic range-finder with a range of forty feet which can be calibrated to a linear voltage output of zero to five volts. The closer an object is to the sensor, the lower the voltage output (e.g. amplitude modulated voltage output wherein 40 ft=5V and 1 ft=0V). In contrast, the nervous system of a subject typically communicates electrical signals via constant amplitude pulses called action potentials, wherein the magnitude of the signal is roughly proportional to the frequency of the pulses, in a current pulse train.

Figure 3:
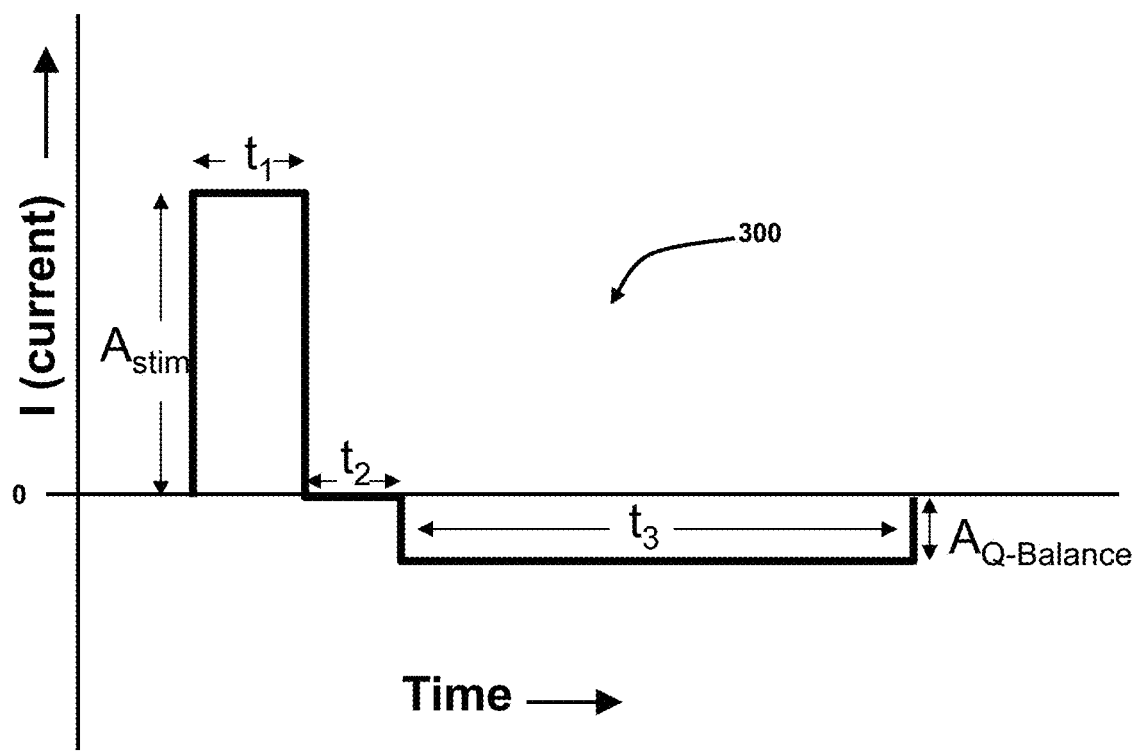
FIG. 3 is a schematic block diagram of an embodiment of a biphasic neural stimulus signal according to the present invention.
Figure 3:
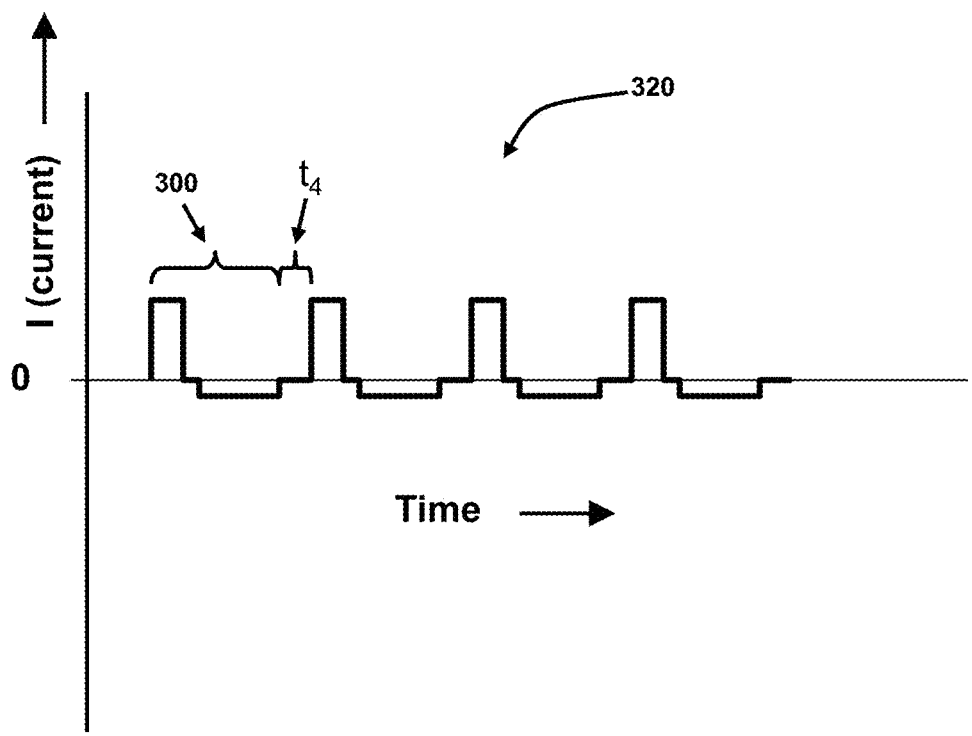

FIG. 3 is a schematic block diagram of a stimulation pulse, also referred to as a biphasic pulse, as can be delivered via an electrode or electrode array to one or more sites located on peripheral nerves within the subject. To simulate action potentials in the peripheral nerves of a subject, an amplitude-modulated sensor output voltage is translated to a frequency-modulated current pulse train. Each stimulation pulse 300 consists of a depolarizing pulse ($A_{stim}$, $t_1$), (pulse current, pulse duration) that generates a potential across the nerve cells' membrane, creating an action potential, and a repolarizing pulse ($A_{Q-balance}$, $t_3$) to rebalance the charge across the membrane, with a time delay ($t_2$) therebetween. The optimal magnitude and duration of these pulses depends on the placement of the electrode in the nerve bundle and the type of neuron(s) the electrode contacts. A calibration procedure can be performed after implantation of an electrode to determine the optimal pulse shapes, as defined for example, by the pulse shape parameters ($A_{stim}$, $t_1$, $t_2$ $A_{Q-balance}$, $t_3$) for each subject and electrode-peripheral nerve site location. These pulse shape parameters can additionally be stored in a memory incorporated in a processor sub-module 234, of in-vivo module 230, as illustrated in FIG. 2. As described below, storing parameterized representations of stimulation waveforms in a memory within the in-vivo module 230, greatly reduces the required downlink bandwidth for communicating stimulation commands between the ex-vivo module 220 and the in-vivo module 230.

In exemplary embodiments of the invention, the temporal spacing of the stimulation pulses 300 are varied with a time spacing ($t_4$) between each repeated stimulation pulse 300 to create a frequency-modulated pulse train 320 based upon the output of the sensor module 210. The magnitude of the voltage signal transmitted by the sensor module 210 can be scaled to the time delay ($t_4$) between pulses 300. For the exemplary range finder, a larger signal from the sensor resulted in a longer time delay and thus a lower frequency pulse train (e.g. larger $t_4$). Algorithms to translate the amplitude-modulated sensor output voltage to a frequency-modulated current pulse train can be implemented for example, in LabVIEW™, a commercial software tool available from National Instruments Corporation, Austin, Tex., USA. In the exemplary embodiment, the range finder signal was acquired by a personal computer via an analog to digital (A to D) board and was processed to generate a frequency-modulated stimulating pulse. Values for the pulse shape parameters in the present example, wherein a laboratory rat was the intended subject, are expected to lie within the approximate ranges:

$A_{stim}$≈+/−35 µA in 2.19 µA steps,
$A_{Q-balance}$≈+/−35 µA in 2.19 µA steps,
$t_1$≈50 µs to 400 µs in 50 µs steps,
$t_2$≈25 µs to 200 µs in 25 µs steps,
$t_3$≈300 µs to 2400 µs in 300 µs steps and,
$t_4$≈10 ms to 1000 ms (e.g. 1 to 100 pulses per second).

Referring again to FIG. 2, the translation algorithm can be implemented in the ex-vivo module 220 as a compact electronics package strapped to the subject. The sensor module 210 can be located remotely from the subject or, can as well be strapped to the subject. A commercial radio transmit-receive module, such as the LINX™LR series available from Linx Technologies INC, Merlin, Oreg., USA, can be used to wirelessly transmit information from the sensor module 210 to the ex-vivo module 220. A microcontroller within sensor processing sub-module 218 can be used to convert the analog output of the sensor element 214 into a digital signal to be communicated via the transmit-receive sub-module 216 to ex-vivo transmit-receive sub-module 222. A microcontroller within ex-vivo processor sub-module 224 can be utilized to translate the sensor signal into a frequency-modulated current pulse train (e.g. 320 in FIG. 3). The frequency-modulated current pulse train can then be used to drive an inductive coil (e.g. 228b) that is part of the inductive coupling 228, the transcutaneous wireless communication link to the in-vivo module 230.

In the exemplary embodiment of the invention, in-vivo module 230 can comprise a transmit-receive sub-module 232 for communication with the ex-vivo module 220 via the inductively coupled link 228, a processor sub-module 234 and battery sub-module 236. Processor sub-module 234 can include for example a microcontroller or ASIC (Application Specific Integrated Circuit) configured to process the stimulation commands sent by the ex-vivo module 220.

Commands transmitted to the in-vivo module 230 include selecting site addresses (e.g. electrode-neuron locations) for stimulation of neurons, or recording of neural responses at particular times, settings of stimulation properties (e.g. waveform parameters) and commands for communications diagnostics. In the present exemplary embodiment, commands can be communicated digitally via the inductive link 228 as combinations of 1 MHz and 2 MHz pulses, using a frequency-shift-keyed (i.e. FSK) technique. In this implementation of the FSK technique, each digital bit of transmitted information consists of two pulses at 1 MHz and two pulses at 2 MHz, where the order of the pulses determines the value of a logic bit; thus the input bitrate is approximately 333 kbps. For example, a logic "0" consists of two pulses at the first frequency, followed by two pulses at the second frequency, and a logic "1" consists of two pulses at the second frequency followed by two pulses at the first frequency. When the frequency shifts the first pulse at the new frequency is subject to error (e.g. due to phase lag) but the second pulse is very accurate. In embodiments of the present invention, the first pulse is ignored and only the second pulse (i.e. the second and fourth pulse in each logic bit) is used to determine logic "0" or logic "1", thus making transdermal methods for communicating information from the ex-vivo module 220 to the in-vivo module 230 according to the present invention, very reliable and robust.

Storing parameterized representations of stimulation waveforms in a memory within the in-vivo module 230 (e.g. illustrated in sub-module 234) greatly reduces the required downlink bandwidth for communicating stimulation commands between the ex-vivo module 220 and the in-vivo module 230. By storing parameterized waveforms in memory, a stimulation command from the ex-vivo module 220 to the in-vivo module 230 only need include site location and "start" stimulation command, and need not include a series of time steps and amplitudes to define the waveform, thus greatly reducing the amount of information that need be communicated across the inductively coupled link 228. To illustrate the advantage of utilizing stored parameterized waveforms in embodiments of the invention, consider a non-limiting example where a stimulation waveform is 10 ms long and comprises 50 µs steps. To communicate the waveform (e.g. a non-parameterized waveform) can require 2 bits to command the in-vivo module to stimulate, plus 5 bits to set the pulse amplitude, plus 3 bits to identify the site location, with a 50 µs step this yields a 200 kbps bandwidth requirement {i.e. 200 kbps=(2+5+3 bits)/50 µs}. By contrast, where a parameterized waveform is stored in a memory, the command need only communicate the site location at 10 ms intervals which yields 2 bits to command the in-vivo-module to stimulate, plus 3 bits to identify the site location which yields a 0.5 kbps bandwidth requirement {i.e. 0.5 kbps=(2+3 bits)/10 ms}. This represents a reduction in required bandwidth by a factor of 400 {i.e. 400=200 kbps/0.5 kbps} by utilizing parameterized waveforms.

The inclusion of battery sub-module 236 (e.g. comprising one or more batteries, or a battery pack) within the in-vivo module 230 allows for incorporating a sensitive receiving circuit in the internal transmit-receive sub-module 232 which is designed to detect pulses with amplitudes in the low mV range. This accommodates significant uncertainty in the efficacy of the coupling through the skin 280 of the subject and provides the ability to accurately read inductively transmitted data with low voltage amplitude. For example, the input stage of the implanted transmit-receive module 232 can include a battery powered multistage amplifier comprising wideband amplifiers and a current starved inverter. This configuration in the amplifier chain operates on a very small input sinusoid and amplifies it into a square wave, for communications implementing FSK. Transdermal communication methods according to the present invention, between ex-vivo module 220 and in-vivo module 230 can be accomplished by a transmitted signal having an amplitude on the order of twelve volts or less (with some embodiments expected to operate on approximately 5 volts) thereby minimizing heating effects on the skin (i.e. due to the low voltage) with a low error rate (i.e. due to FSK encoding) while also minimizing the size and weight of the ex-vivo hardware utilized to generate the signals. Transdermal communication methods according to the present invention including incorporation of an in-vivo battery, avoid skin heating effects and complications that can arise from energy harvesting approaches to operating an in-vivo module.

Ex-vivo module 220 can for example, transmit an encoded (FSK) command to in-vivo module 230 that includes site location(s) for neural stimulation and the magnitude of the stimulation, i.e. the frequency or repetition rate of the frequency-modulated pulse train. In-vivo processor sub-module 234 can be configured to decode (i.e. recover) the encoded information and convert that information into electrical neural stimuli comprising the frequency-modulated train of stimulation pulses having pulse shapes as determined from the pulse shape parameters (see FIG. 3) that can be stored in memory within the processor sub-module 234. Electrical neural stimuli generated by processor sub-module 234 are then delivered to the specified peripheral nerve sites 250 by the in-vivo electrode 240.

The utilization of an implanted electrode 240 (e.g. a point electrode, an electrode array, a microelectromechanical (MEM) electrode array) to stimulate peripheral nerve sites 250 (e.g. a nerve or nerve bundle) avoids the use of percutaneous wires or connectors, reducing the risk of irritation and infection and makes embodiments of the present invention amenable to chronic (e.g. long-term) use.

In-vivo electrodes 240 can include for example, those commercially available from NeuroNexus Technologies, Ann Arbor, Mich., USA.

Exemplary of bidirectional communication, ex-vivo module 220 can additionally transmit an encoded command to in-vivo module 230 that includes site location(s) for neural response recording, which can be used to facilitate set-up and calibration of a neural interface, including determining optimal stimulation pulse shapes (e.g. pulse shape parameters as in FIG. 3). In recording a neural response (e.g. action potential) electrical signals received by the in-vivo electrode 240 are passed to the processor sub-module 234. An analog to digital converter (ADC) within processor sub-module 234 can be used to digitize the neural response which can be stored in memory within the processor sub-module and communicated to ex-vivo module 220 via the inductively coupled link 228. As "up-linked" communications from in-vivo module 230 to ex-vivo module 220 typically do not require the high degree of accuracy or the high data rates desired for "down-linked" commands sent to the in-vivo module 230 from the ex-vivo module 220, up-linked communications can be transmitted in a simple Manchester encoded format. In embodiments utilizing this approach, inductively coupled link 228 can comprise two sets of proximal coils as illustrated in FIG. 2, one set for FSK encoded down-linked communications, and a second set for Manchester encoded up-linked communications. This additionally provides a capability for simultaneous and bidirectional communication between ex-vivo 220 and in-vivo 230 modules.

In-vivo battery sub-module 236 can include a battery charging circuit that can be inductively coupled to an optional external (i.e. ex-vivo) battery charging module 260, to provide a wireless recharging capability for the in-vivo battery. In an exemplary embodiment, an in-vivo chip inductor can be used for wireless battery charging, which requires a sufficient voltage in a corresponding coil 228e outside the skin to induce approximately 3V at an in-vivo coil (e.g. 228d). The necessary voltage can be dependent on the specific details of the battery and battery charging circuit, as well as the coupling between external and internal coils comprising the inductively coupled charging link, which in turn can depend on the placement of the in-vivo module 230. The in-vivo battery charging circuit sub-module 236 can be configured to rectify and smooth input waveform, boost the voltage with a charge pump and utilize a current mirror to produce a constant current charge of approximately 1.5 mA. In embodiments of the invention with the in-vivo processor sub-module 234 powered off, it is estimated that internal batteries can be charged in approximately three hours. Thus the internal battery can be charged while the subject is in proximity to a higher-voltage amplifier (e.g. while the subject sleeps) but such voltages are not required for regular operation. In some embodiments of the invention, inductively coupled coils (e.g. 228b,c) can be utilized for multiple functions, such as for battery charging and down linked data communication.

Figure 4:
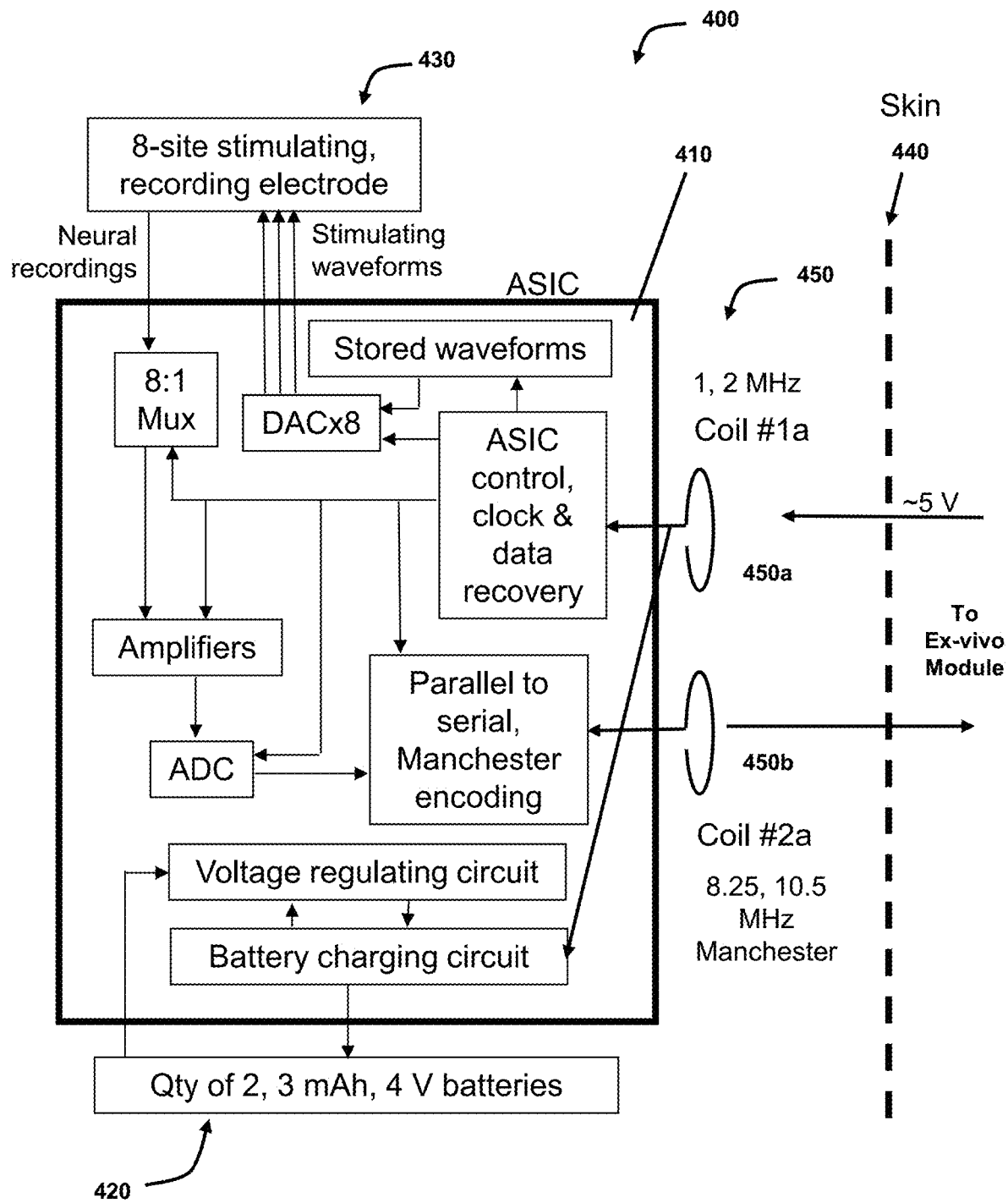
FIG. 4 is a schematic block diagram of an embodiment of an implantable (in-vivo) module and electrode array according to the present invention.

FIG. 4 is a schematic block diagram of an embodiment of an implantable (in-vivo) module and electrode array according to the present invention. This embodiment of an implantable, in-vivo module 400 for use in neural interfaces, takes advantage of Application Specific Integrated Circuit (i.e. ASIC) technology to incorporate the bulk of the functionality required of an in-vivo module into a single IC (integrated circuit), ASIC 410. Inter alia, the use of ASIC 410 minimizes the size of the implanted in-vivo module 400. The ASIC communicates to an ex-vivo module over an implantable inductively coupled telemetry link 450 that can comprise implanted chip inductors (450a,b) for example as commercially available from Coilcraft Inc., Cary, Ill., USA, and can be powered by implantable batteries 420, for example as commercially available from Quallion LLC, Sylmar, Calif., USA. The ASIC can operate in three different modes: neural stimulation, neural signal recording and data link check. In stimulation mode the ASIC can deliver up to approximately +1-35 µA in 5 bit steps to neural stimulation sites (via electrode 430) having impedances of less than approximately 50 kΩ. The amplitude, duration, and location of each neural stimulation pulse can be programmed wirelessly across the transcutaneous link 450. The input stage of the implantable receiver is a multistage amplifier consisting of two wideband CMOS (complimentary metal oxide) amplifiers and a current starved inverter. This amplifier chain takes a very small input sinusoid and amplifies it into a square wave. The chip operates using frequency shift Keying (FSK) down-linked communications and Manchester encoded up-linked communications.

In FSK encoded down-linked communications each bit is represented by a succession of four pulses at either 2 MHz or 1 MHz. If the two 2 MHz pulses are sent first, a logic 0 is received and sending the two 1 MHz pulse prior to the 2 MHz pulses results in a logic 1. Sending no pulses for greater than 5 µs resets the chip and places it in data link check mode, where the chip transmits every bit it receives back out of the subject on the inductively coupled transcutaneous link 450. The circuit used to discriminate between the two logic levels first divides the input pulses by two, to determine the total duration of each pulse and, the first pulse at each at each frequency is thrown out due to a potential error in its duration due to the slightly under damped receiver and transmitter tank circuits. During the second pulse at each frequency, a capacitor is charged or discharged by a constant current to determine whether the second or fourth pulse is longer. A comparator then turns the voltage levels at the outputs of the two capacitors into logic levels and the voltages across the capacitors are reset and ready to receive another bit. An advantage of this approach is that it is immune to offsets in the input amplifier and noise in the environment. Since very small signals can be processed, the operating length of the transcutaneous link 450 can be much greater than previous inductively coupled systems and the bit error rates are expected to be much lower.

The ASIC 410 can also be used to record neural activity from the peripheral nervous system (PNS). A multiplexer first selects the preprogrammed site to record. This signal is amplified by a low-noise neural recording amplifier and quantized to ten bits of resolution. The back telemetry to an ex-vivo module is achieved using the on/off frequency shift keying of an on-chip 7 MHz oscillator (e.g. Manchester encoding) using a separate back telemetry tank circuit. Each functional module within the ASIC 410 is powered down when not in use. Regardless of operating mode, it is estimated that the ASIC 410 can be operated for greater than eight hours from two implantable 3 mAh batteries.

In this exemplary embodiment, one chip inductor (450a) can be utilized for down-linked communication as well as battery charging functions, and a second chip inductor (450b) can be utilized for up-linked communications. Scale mock-ups of the in-vivo module 400 (excluding electrodes 430) indicate the size of the implanted module is quite modest, and can be accommodated in an implantable oval form factor, measuring approximately 3.5 cm×2.2 cm×0.5 cm thick. Packaging of the in-vivo module 400 (excluding electrodes 430) can be accommodated in ceramic-hermetic technologies such as low-temperature co-fired ceramic (LTCC), commercially available as DUPONT™ GREEN TAPE™, from DuPont, Research Triangle Park, NC, USA, with connections to the electrode array 430 protected by polymer epoxy.

Figure 5:
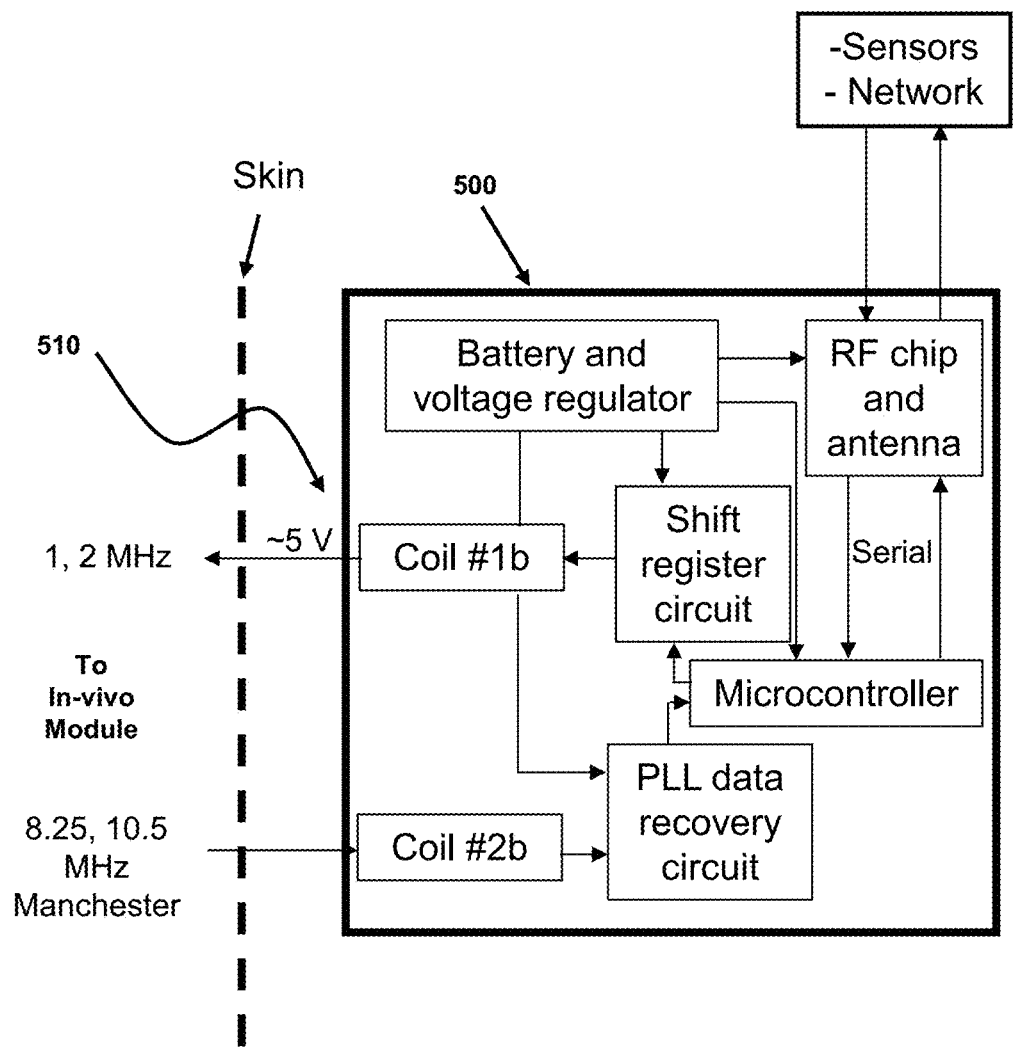
FIG. 5 is a schematic block diagram of an embodiment of an external (ex-vivo) module according to the present invention.

FIG. 5 is a schematic block diagram of an embodiment of an external (ex-vivo) module according to the present invention. Ex-vivo module 500 includes a microcontroller that communicates serially via an RF chip for communication to sensor nodes and optional computer network. The microcontroller additionally manages communication with an in-vivo module through two dedicated circuits, one for transmitting and one for receiving. The transmit circuitry translates serial data into the necessary sequences of 1 MHz and 2 MHz pulses for FSK communication and drives the inductor circuit. The receive circuitry amplifies the Manchester up-linked communication signals to a detectable level and identifies the data frequencies. The microcontroller generates stimulation patterns, limiting them to a safe, predetermined set of values. A battery pack powers the ex-vivo module 500.

The physical configuration of the ex-vivo module 500 can be arranged to accommodate attachment to the subject and proximity to the in-vivo module, for example, to optimize the coupling of inductive link 510. The ex-vivo module can be attached to the subject mechanically, or with adhesive. The total volumes of embodiments of the ex-vivo module can be on the order of a few cubic inches, require power of approximately 300 mW from a 5V source, and can communicate to external sensors or network at distances of up to 500 ft.

Figure 6:
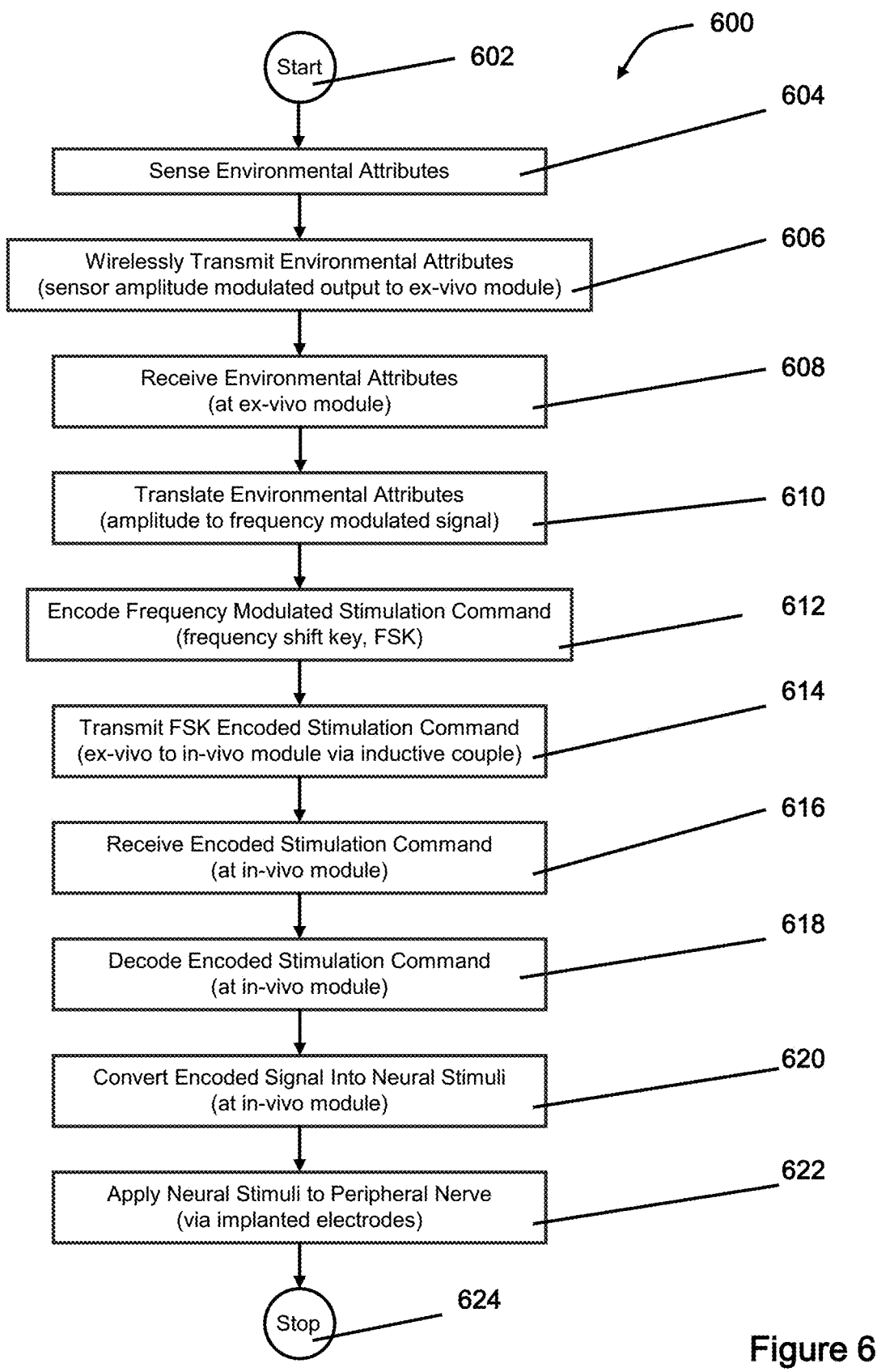
FIG. 6 is a schematic block diagram of an embodiment of a method according to the present invention, for operating a neural interface to provide an artificial sensory capability to a subject.

FIG. 6 is a schematic block diagram of an embodiment of a method according to the present invention, for operating a neural interface to provide an artificial sensory capability to a subject. The method 600 starts at step 602, and can be practiced for example, on embodiments of neural interfaces and the functionalities therein, such as described above for FIGS. 1 through 5. At step 604 one or more sensor modules sense attributes of an environment within which a subject is operating, that are outside the natural capabilities of the subject. At step 606 the sensor module(s) transmit the attributes to an ex-vivo module mounted on a subject. The attributes can be transmitted as an amplitude-modulated signal corresponding to the magnitude of the output from a sensor(s). At step 608 the ex-vivo module receives the sensed attributes from the sensor module(s). At step 610 the ex-vivo module translates the amplitude-modulated sensor output(s) into a frequency-modulated signal, compatible with the peripheral nervous system of the subject. At step 612 the ex-vivo module can encode the frequency-modulated stimulation signal, by a frequency-shift-key technique (FSK). At step 614 the ex-vivo module can transmit the encoded stimulation signal (e.g. command) across an inductively coupled transcutaneous link to an in-vivo module. At step 616 the in-vivo module can receive the FSK encoded stimulation signal. At step 618 the in-vivo module can decode the encoded stimulation signal. At step 620 the in-vivo module can convert the stimulation signal into electrical neural stimuli that are delivered to sites located on a peripheral nerve of the subject at step 622, by an implanted electrode. The method ends at step 624.

Figure 7:
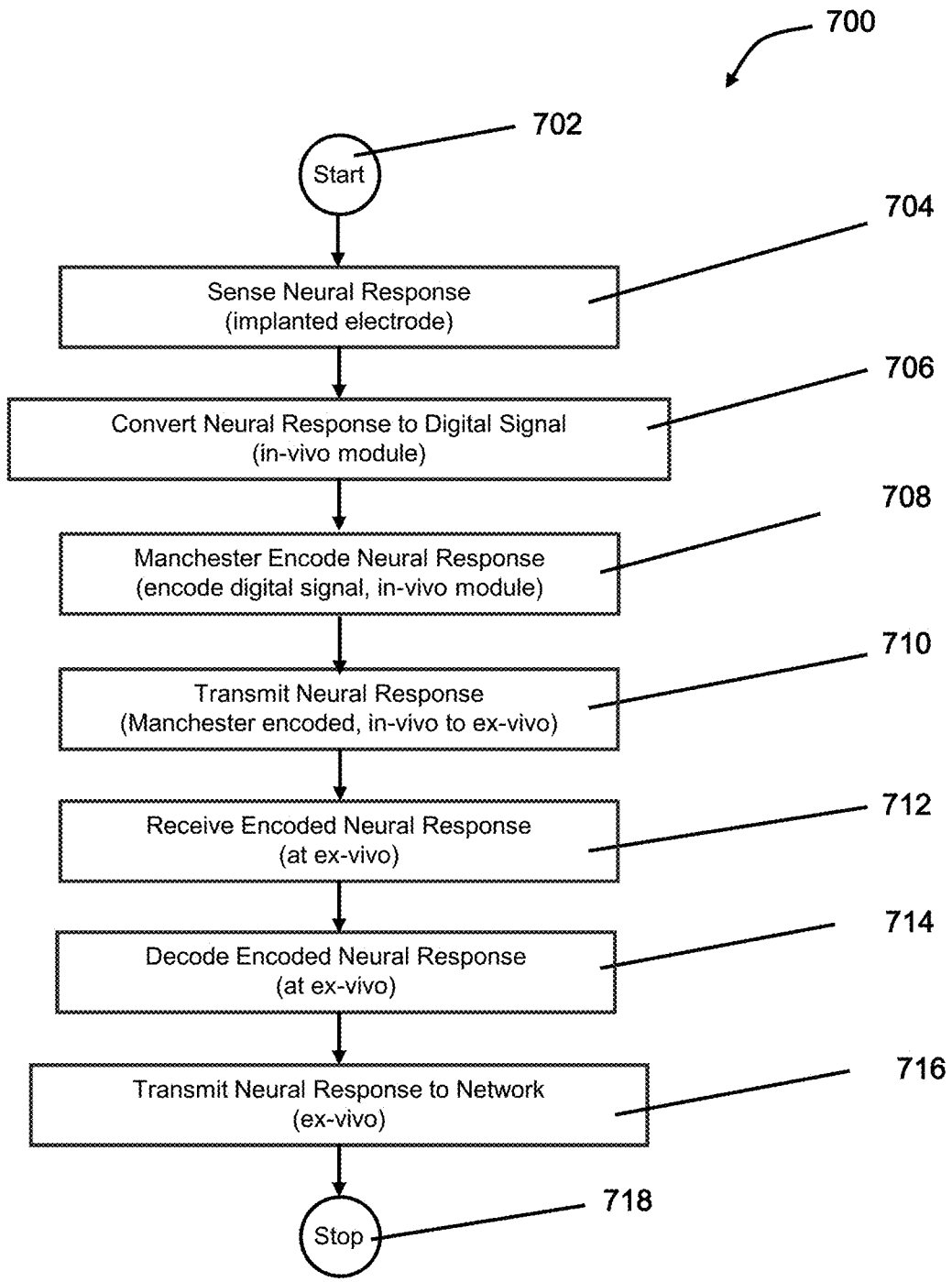
FIG. 7 is a schematic block diagram of an embodiment of a method according to the present invention, for operating a neural interface to obtain a neural response from a subject.

FIG. 7 is a schematic block diagram of an embodiment of a method according to the present invention, for operating a neural interface to obtain a neural response from a subject. The method 700 starts at step 702, and can be practiced for example, on embodiments of neural interfaces and the functionalities therein, such as described above for FIGS. 1 through 5. At step 704 a neural response (e.g. action potential) is detected by an implanted electrode, contacting peripheral nerve sites within the subject, and conveyed to an in-vivo module. At step 706 the in-vivo module converts the analog neural response into a digital signal. At step 708 the in-vivo module encodes the digitized neural response by a Manchester encoding algorithm. At step 710 the in-vivo module transmits the Manchester encoded digitized signal to an ex-vivo module, via an inductively coupled transcutaneous link. At step 712 the ex-vivo module receives the encoded neural response. At step 714 the ex-vivo module decodes the encoded neural response to recover the digitized form of the neural response. At step 716 the ex-vivo module can transmit the neural response to an (optional) external network, which can comprise a computer. The method ends at step 718. Embodiments of neural interfaces according to the present invention can practice the methods as described in FIGS. 6 and 7 simultaneously, thereby providing a bidirectional transcutaneous communication capability, between in-vivo and ex-vivo modules as may comprise a neural interface.

The above described exemplary embodiments present several variants of the invention but do not limit the scope of the invention. Those skilled in the art will appreciate that the present invention can be implemented in other equivalent ways. The actual scope of the invention is intended to be defined in the following claims.

What is claimed is:

1. A method for operating a neural interface to provide an artificial sensory capability to a subject, the artificial sensory capability providing information to the subject obtained from sensors operating outside the natural sensory capabilities of the subject, the method comprising:
   sensing by a sensor module an attribute of an ex-vivo environment within which the subject is operating, the attribute being outside the natural sensory capability of the subject, the sensor module comprising a sensor transmitter;
   transmitting wirelessly the attribute by the sensor transmitter;
   receiving the attribute by an external module mounted ex-vivo on the subject;
   translating the attribute by the external module into a neural stimulation command;
   encoding the neural stimulation command by the external module;
   transmitting the neural stimulation command by the external module;
   receiving the neural stimulation command wirelessly by an internal module mounted in-vivo to the subject via an inductively coupled link;
   decoding by the internal module the neural stimulation command to recover the neural stimulation command;
   converting the neural stimulation command into an electrical neural stimulus by the internal module; and
   conveying the electrical neural stimulus to one or more neurons within the subject by an electrode mounted in-vivo to the subject so the subject senses the attribute, the electrode electrically connected to the internal module and electrically contactable to the one or more neurons;
   wherein the attribute of the ex-vivo environment is selected from a group consisting of range to an object, wavelengths of light outside of visible light wavelengths, radiation, chemical data analysis, sound outside of human hearing frequency, forces and accelerations acting on a remote vehicle and a human characteristic of another; and wherein the human characteristic of another is selected from a group consisting of vital signs, coristol levels, EEG measurements and galvanic skin response.

2. The method of claim 1, wherein the step of transmitting the neural stimulation command by the external module over the inductively coupled link, further comprises transmitting an electrical signal having a peak-to-peak amplitude on the order of 12 volts or less.

3. The method of claim 1 wherein the electrical neural stimulus comprises a frequency-modulated pulse train of repeating biphasic stimulation pulses.

4. The method of claim 1 wherein the step of decoding by the internal module the neural stimulation command further comprises:

detecting frequency shifts in a sequence of pulses comprising a first frequency and a second frequency; and, discarding each pulse immediately following each frequency shift in the sequence of pulses thereby creating a robust sequence of pulses.

\* \* \* \* \*